United States Patent
Cron et al.

[11] Patent Number: 6,148,822
[45] Date of Patent: *Nov. 21, 2000

[54] PROPRIOCEPTIVE SOLE OR PEDAL DEVICE CONTAINING CRYSTALS FOR TREATMENT OF STATURAL DISORDERS

[75] Inventors: Christophe Cron, Deroche; Thierry Pautrot, Carignan; Thierry Abribat, Montréal, all of Canada

[73] Assignee: Asana Laboratories, Longueuil, Canada

[*] Notice: This patent is subject to a terminal disclaimer.

[21] Appl. No.: 09/204,300

[22] Filed: Dec. 3, 1998

Related U.S. Application Data

[63] Continuation-in-part of application No. 08/642,634, May 2, 1996, abandoned.

[51] Int. Cl.[7] ................................................ A61B 19/00
[52] U.S. Cl. ............................................................ 128/897
[58] Field of Search ........................... 36/43.91; 128/898, 128/897; 132/73

[56] References Cited

U.S. PATENT DOCUMENTS

| 5,158,526 | 10/1992 | Bricot . | |
| 5,766,596 | 6/1998 | Kwon | 424/195.1 |
| 5,884,639 | 3/1999 | Chen | 132/321 |
| 5,913,313 | 6/1999 | Brunderman | 132/76.4 |
| 6,024,093 | 2/2000 | Cron et al. | 128/897 |

*Primary Examiner*—Linda C. M. Dvorak
*Assistant Examiner*—R. Kearney
*Attorney, Agent, or Firm*—Swabey Ogilvy Renault; France Côté

[57] ABSTRACT

The present invention relates to an article such as a sole or a shoe adapted to contact the sole of a foot, which incorporates at least one unoriented mineral which is capable of developing a color in the wavelength range between about 400 nm and 900 nm and stimulates the reflex zones located at the sole of the foot. The method of utilizing such article is also disclosed.

21 Claims, 5 Drawing Sheets

Fig. 8  Mean ± SEM of postural scores of 96 patients without (BASAL) and with (MINERAL) the mineral insoles (P<0.001)

a: P<0.01 when compared to Basal score
b: P<0.05 when compared to Basal 1 score
c: P<0.01 when compared to Mineral 1 score Fig. 9  Mean ± SEM of postural scores of 22 patients tested before and after one month of chiropractic treatment (Before chiropractic treatment: Basal 1 -without insoles- and Mineral 1 -with mineral insoles-; After chiropractic treatment: Basal 2 -without insoles- and Mineral 2 -with mineral insoles-)

PROPRIOCEPTIVE SOLE OR PEDAL DEVICE CONTAINING CRYSTALS FOR TREATMENT OF STATURAL DISORDERS

RELATED APPLICATIONS

This application is a continuation-in-part of application serial number 08/642,634 filed on May 2, 1996 which is now abandoned and herein incorporated by reference.

BACKGROUND OF THE INVENTION (a) Field of the Invention

The present invention relates to medical devices and a therapeutic method for the treatment and the prevention of physical troubles associated with a statural disequilibrium.

(b) Description of Prior Art

A major part of the chronic pains of the back or of the neck are caused by spine disequilibrium. This disequilibrium is clinically associated with imbalances or rotations of the pelvic and pectoral girdles.

It has been documented that less than 10% of the population has perfectly balanced pelvic and pectoral girdles, i.e., an equilibrated spine. Those individuals almost never experience back or neck chronic pain in their life span, and are rarely prone to arthrosis. Constitutive or acquired imbalances occur in the remaining 90% of the population, in whom spine curvatures and intervertebral angles are non-physiologic, leading to pain, sequentially at the muscular, articular and ultimately the bone level.

Spine disequilibrium may also be responsible for various disorders, including muscular and articular pains, vertigos, lumbagos, arthrosis. The link between these disorders and the spine was established based on observations that correction of the pelvic and pectoral girdles imbalances resulted in improvements of the symptoms.

Various therapeutic approaches have been developed to restore the spine equilibrium, and thus alleviate chronic pains in patients. Most of these approaches involve the design of pedal devices, mainly soles, since the feet are the points of normal support of the body in human. In fact, it has been proven that the feet are the origin of ascending neural proprioceptive chains that control the tonus of the statural muscular system, of which the spine muscles are one component. Adequate stimulations of particular reflex zones located on the sole of the feet induce a realignment of the ascending proprioceptive chains, and thus a re-equilibration of the skeletal muscular system.

This concept has previously been verified by the design of the following types of soles:

soles with micro-reliefs located at the level of the reflex zones of the foot have been used for several years. However, the routine use of this type of sole is hampered by the fact that the micro-reliefs have to be very meticulously adjusted for each patient, and their precise thickness must be regularly modified. In addition, they are only active when the patient is in a standing position.

soles incorporating a polarizing substance, such as a polarizing or polarizer plate have been described in U.S. Pat. No. 5,158,526. These soles have been marketed in Europe for several years and have been used for the correction of statural disorders. However, they exhibit some major drawbacks, that limit their routine clinical use. Namely, they need to be applied continuously directly at the contact of the skin of the foot sole, their efficacy being almost completely abolished when fabrics such as nylon or stained cotton, found in socks or stockings, are placed between the device and the skin. This continuous application induces increased perspiration in most of the patients, which makes them uncomfortable to wear, resulting in a poor patient's compliance. In addition, the lifetime of the active principles of these soles (superposed polarizer plates) is limited to several months, requiring a regular monitoring of the device's efficacy.

a similar kind of soles incorporating at least one flexible filtering film with a determined spectral transmission curve have been described in Canadian patent No. 1,328,734.

Although several case reports have described the efficacy of the aforementioned types of soles, there exist no data from controlled clinical studies performed to establish their clinical usefulness. Despite the fact that anecdotal research, such as case reports, may provide some valuable information on the activity of a product, it is widely recognized by the scientific and medical communities that only placebo-controlled, double blind studies can help to fully objectively assess the efficacy and the safety of such a medical device, especially when the parameters used to measure efficacy are essentially clinical, qualitative or semi-quantitative parameters.

There is described a sole of superposed polarizing plates in U.S. Pat. No. 5,158,526 (in the name of Bricot). Bricot teaches a method and an apparatus for treating reflex zones of feet by applying polarized magnetic flux to the reflex zones of feet. Although, Bricot teaches that microcrystals may be used in his sole, he also teaches the absolute necessity to process said microcrystals into a polarizer under specific conditions such that the crystals are oriented. This polarizer is used to treat reflex zones of the feet.

Therefore, it is an object of the present invention to provide a pedal device without the use of any polarizer, such as a sole, a shoe or another pedal apparatus, that would allow to rapidly correct spine disequilibrium, and thus alleviate associated physical disorders, such as chronic back or neck pains.

It is another object of the invention to provide a type of sole that could exert a therapeutic effect when worn under socks or stockings, in order to prevent patient's discomfort, and therefore improve compliance.

It is also an object of the invention to provide a type of sole, of which the active principles would have a long lifetime, in order to avoid the need for frequent monitoring of the quality of the sole.

It is also an object of the invention to provide a type of sole with a clinical efficacy proven by data resulting from placebo-controlled, double-blind studies.

SUMMARY OF THE INVENTION

The invention relates to a pedal device for treating and/or preventing physical troubles associated with statural disequilibrium, which comprises an article adapted to contact a sole of a foot, said article incorporating within two layers at least one unoriented mineral for stimulating reflex zones located at the sole of the foot, whereby said unoriented mineral does not act as a polarizer.

To the opposite of Bricot (U.S. Pat. No. 5,158,526), in accordance with the present invention, the specific minerals are not oriented such that these crystals are not acting as a polarizer. In fact, the pedal device of the present invention comprises a crystalline substance which is not oriented and processed. In addition, to the opposite of Bricot, the unoriented mineral used in accordance with the present invention do not require to be applied directly in contact with the skin of the foot sole to be active as illustrated in Example I. The pedal device of the present invention has an unlimited lifetime.

In accordance with the present invention, there is also provided a method for treating and/or preventing physical troubles associated with statural disequilibrium which comprises placing a pedal device at one or both feet of a person in need of correction of statural disequilibrium, said pedal device comprising an article adapted to contact a sole of a foot, said article incorporating within two layers at least one unoriented mineral which include, without limitation, sulfur powders, jasper, cornelian, topaz safranite, aventurine, azurite, amethyst and quartz for stimulating reflex zones located at the sole of the foot, whereby treating and/or preventing physical troubles associated with statural disequilibrium, whereby said unoriented crystalline substance does not act as a polarizer.

In accordance with the present invention, there is also provided a method for improving muscle strength and physical performance which comprises placing a pedal device at one or both feet of a person in need of correction of statural disequilibrium, said pedal device comprising an article adapted to contact a sole of a foot, said article incorporating within two layers at least one unoriented mineral which include, without limitation, sulfur powders, jasper, cornelian, topaz safranite, aventurine, azurite, amethyst and quartz for stimulating reflex zones located at the sole of the foot, whereby treating and/or preventing physical troubles associated with statural disequilibrium, whereby said unoriented mineral does not act as a polarizer.

In accordance with the present invention, there is also provided a method for inducing stress relief which comprises placing a pedal device at one or both feet of a person in need of correction of statural disequilibrium, said pedal device comprising an article adapted to contact a sole of a foot, said article incorporating within two layers at least one unoriented mineral which include, without limitation, sulfur powders, jasper, cornelian, topaz safranite, aventurine, azurite, amethyst and quartz for stimulating reflex zones located at the sole of the foot, whereby treating and/or preventing physical troubles associated with statural disequilibrium, whereby said unoriented mineral does not act as a polarizer.

The invention therefore has for its object a pedal device, such as a sole, a shoe or any other pedal apparatus, preferably incorporating one or several types of selected crystals such as minerals possibly in powder form, placed, for example, at designated reflex zones of the foot sole.

The invention also relates to a therapeutic method consisting in using the aforementioned device to achieve a partial or complete restoration of the spine physiological alignment, and therefore prevent or cure physical disorders associated with spine disequilibrium such as musculoskeletal pain.

The invention also relates to a therapeutic method consisting in using the aforementioned device as a therapeutic agent to improve the condition of patients suffering from musculoskeletal pain, such as chronic back pain associated or not with spine disequilibrium.

The active principle of the sole or of the pedal device may be a combination of one or several unoriented minerals, which do not act as polarizer. Both the type and amount of unoriented minerals to be used, alone or in combination, are selected based on their ability to stimulate the reflex zones located at the sole of the foot. Although the exact mechanism involved in alleviating musculoskeletal pains associated or not with spine disequilibrium and troubles associated with statural disequilibrium is not well understood, it is believed that these unoriented minerals produce natural frequencies and radiations which affect the reflex zones. The unoriented minerals may be mono-, bi-, or multi-atomic, preferably in the form of powders or crystals. They may be selected from the following groups which are listed as illustrative examples:

elements in crystal or powder forms, such as diamond (C), gold (Au), copper (Cu), platinum (Pt), sulfur (S or $S_8$), silver (Ag), or bismuth (Bi);

natural and synthetic sulphides and sulphosalts in the form of crystals or powders, such as argentite (AgS), arsenopyrite (FeAsS), arsenic trisulfide ($As_2S_3$), proustite ($Ag_3AsS_3$), pyrite ($FeS_2$);

natural and synthetic halides in the form of crystal or powders, such as fluorite ($CaF_2$) or cryolite ($Na_3AlF_6$);

natural and synthetic oxides and hydroxides in the form of crystals or powders, such as silicon dioxide ($SiO_2$) derivatives (quartz, jasper, topaz safranite, cornelian, aventurine, amethyst, chalcedony, agate, crystobalite, flint, sand, tridymite) or rutile ($TiO_2$);

natural and synthetic nitrates, carbonates and borates in the form of crystals or powders, such as malachite ($Cu_2[(OH)_2CO_3]$), azurite ($Cu_3[OH/CO_3]$), cerusite ($PbCO_3$);

natural and synthetic sulfates, chromates, molybdates and tungstates in the form of crystals or powders, such as crocoite ($PbCrO_4$) or anglesite ($PbSO_4$);

natural and synthetic phosphates, arseniates and vanadates in the form of crystals or powders, such as apatite ($Ca_5[F(PO_4)_3]$);

natural and synthetic silicates in the form of crystals or powders, such as Feldspars ($AlSi_3O_8$ and $AlSi_2O_6$ derivatives), micas ($AlSi_3O_{10}$ and $Si_4O_{10}$ derivatives);

natural and synthetic organic substances in the form of crystals or powders, such as amber ($C_{10}H_{16}O$) or aurin ($C_{19}H_{14}O_3$).

The pedal device according to the invention consists in a pedal support device which may incorporate selected crystals or powders (the active principle). The crystals or powders can be inserted either inside or at the surface of the device, provided they are at the level of the sole.

The therapeutic method according to the invention consists in applying the pedal device, either at one or at both feet of the patient, in order to induce the expected therapeutic effect. According to this therapeutic method, the active principle (e.g., the crystals or powders), possibly due to the natural frequencies and radiations they give out, exert a non-toxic stimulatory action on the reflex zones located at the level of the sole skin, thereby stimulating the proprioceptive ascending chains, and inducing an harmonization of the tonus of the statural muscular system. The observed therapeutic effects include the followings:

a rapid re-equilibration of the spine towards normalization of spine curvatures and intervertebral angles, which can be clinically evidenced by disappearance of imbalances, tilts and rotations of the pelvic and scapular girdles.

the relief of symptoms associated with spine disequilibrium, including chronic back and neck pains, other muscular and articular pains, vertigos, lumbagos, arthrosis.

the prevention of the occurrence of the aforementioned disorders associated with spine disequilibrium.

an energetic action, including an increase of physical performances and a diminution of the stress level.

The device according to the invention is notable for the fact that it can exert its therapeutic effect whether applied directly at the contact of the skin of the foot sole or under socks or stockings, made of any type of fabric, which improves patient's comfort and compliance. It is also notable for the fact that its active principle (e.g., the crystals or powders) have an unlimited lifetime, which eliminates the need to frequently monitor the quality of the device. In addition, since the crystals or powders used are naturally occurring on earth, no toxic effect can result from the energy, frequencies or radiations they give out.

BRIEF DESCRIPTION OF THE DRAWING

This invention is illustrated by means of the annexed drawings which are given only for the purpose of illustration and without restriction. In the drawings.

DESCRIPTION OF PREFERRED EMBODIMENTS

Figures 1, 2:
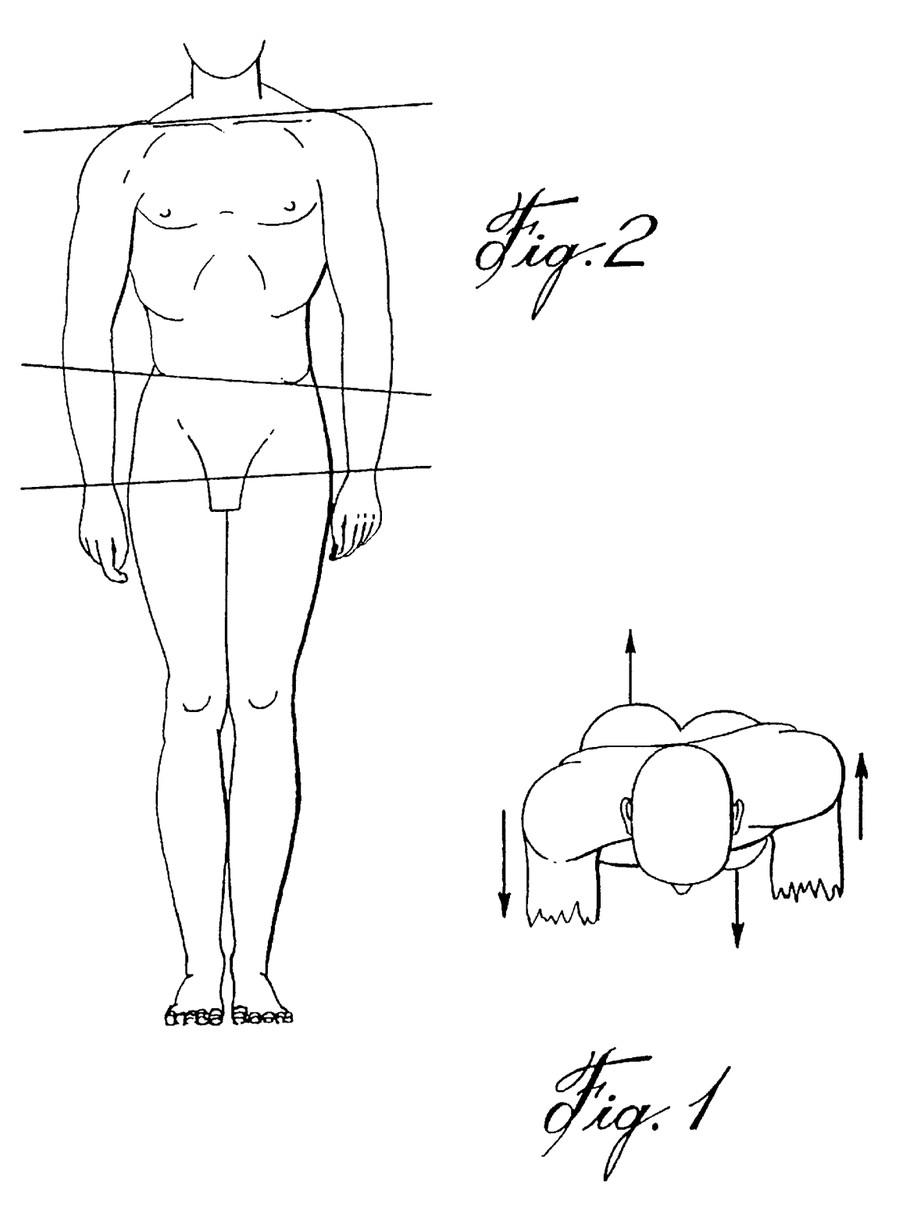
FIG. 1 is an illustration of the rotation of the pectoral and pelvic girdle.
FIG. 2 is an illustration of the imbalance of the pelvic and pectoral girdles.

Two examples of rotations and imbalances are illustrated respectively in FIG. 1 and FIG. 2. FIG. 1 deals with an improper rotation of the pectoral and pelvic girdle and FIG. 2 shows an imbalance of the pelvic and pectoral girdles.

According to a preferred embodiment, the unoriented mineral used as active principle in the pedal device is sulphur in the powder form. According to another preferred embodiment, the active principle is a combination of seven types of crystals or powders, namely red jasper, cornelian, topaz safranite, aventurine, azurite, amethyst and white quartz. According to another preferred embodiment, the active principle is a combination of sulphur in the powder form and the seven minerals previously mentioned in the form of crystals.

Figure 3:
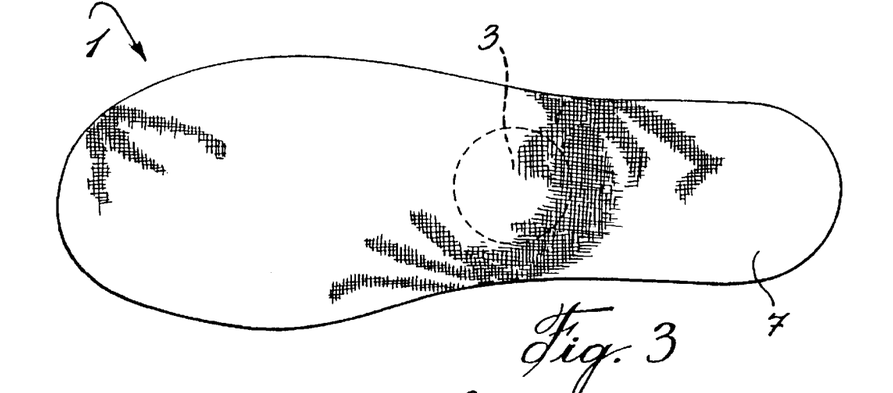
FIG. 3 is a top view of a sole according to the invention including sulphur powder between the two semi-rigid fabric layers.
Figure 4:
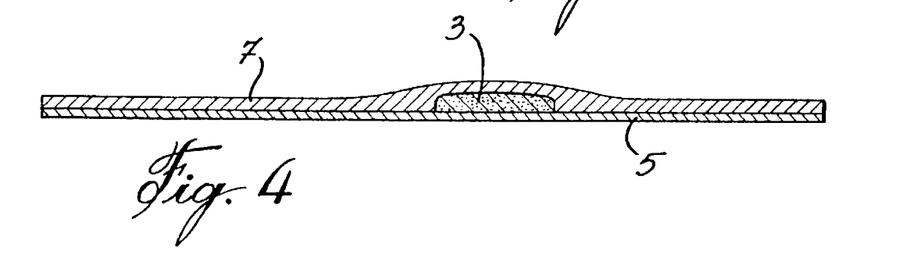
FIG. 4 is a longitudinal cross-section view of the sole illustrated in FIG. 3.

According to a highly preferred embodiment, the pedal device is a sole 1, in which an amount of 5 mg to 30 g of sulphur powder 3 is incorporated at the level of the arch, between the two semi-rigid fabric layers 5 and 7 used to manufacture the sole, as shown in FIGS. 3 and 4 of the drawings.

According to another highly preferred embodiment the pedal device is a sole in which a combination of seven crystals with defined colors (one red, one orange, one yellow, one green, one blue, one purple, and one white) is inserted between the two semi-rigid fabric layers used to manufacture the sole.

Figure 5:
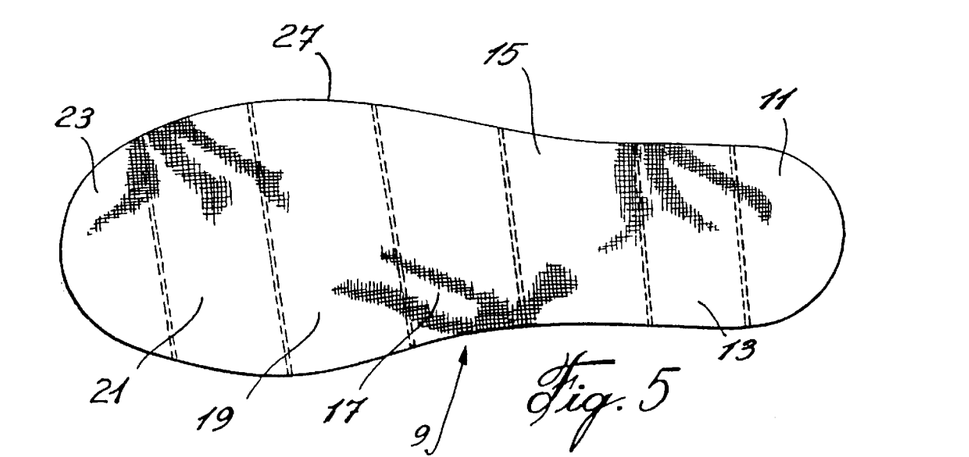
FIG. 5 is a top view of a sole according to the invention including transverse bands of seven different minerals.
Figure 6:
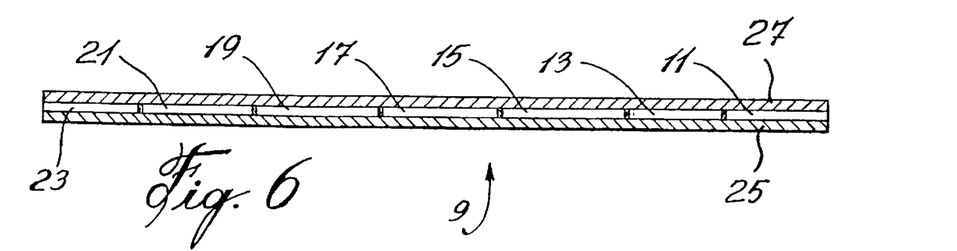
FIG. 6 is a longitudinal cross-section view of the sole illustrated in FIG. 5.

According to another highly preferred embodiment, the pedal device is a sole 9, in which a combination of seven different crystals or powders with selected colors (red jasper 11, orange cornelian 13, yellow topaz safranite 15, green aventurine 17, blue azurite 19, purple amethyst 21 and white quartz 23) is inserted as seven bands transversely between the two semi-rigid fabric layers 25, 27 used to manufacture the sole, as shown in FIGS. 5 and 6 of the drawings.

According to another highly preferred embodiment, the pedal device is a sole, in which both the sulphur powder and the combination of the seven crystals are incorporated.

The present invention will be more readily understood by referring to the following examples which are given to illustrate the invention rather than to limit its scope.

EXAMPLE I

Effects of Soles Containing Sulphur vs. Soles with Polarizing Polaroid™ Plates on Patient's Stature Placebo-controlled, Double-blind Studies The goal of this study was to assess the efficacy of sulphur-containing soles and to compare it to that of soles containing a previously described (U.S. Pat. No. 5,158,526) active principle, i.e., superposed polarizing plates. Efficacy was judged clinically by the ability of tested soles to correct imbalances and rotations of the pectoral and the pelvic girdles. In study A, soles were tested immediately at the contact of the feet skin, whereas in study B, soles were tested under socks. Both studies were run in a double-blind fashion vs. a placebo sole, in order to prevent any subjective component in the course of the clinical evaluation.

Materials and Methods

Patients:

A total of 40 patients (24 in study A and 16 in study B) were included in the protocols. Selected patients ranged between 18 and 65 years of age, and had imbalances of the pectoral and of the pelvic girdles, as evidenced in an initial clinical evaluation. None of them had received any kind of medical sole in the previous 6months.

Treatments:

Three pairs of soles were designed for the needs of the present studies. The first one was a sole, in which an amount of 50 to 100 mg of sulphur powder was incorporated at the level of the arch, between the two semi-rigid fabric layers used to manufacture the sole, according to one of the preferred embodiment of the present invention. The second one was a sole made with the active principle (superposed Polaroid Tm plates) commercialized by the company Statipro (Marseille, France), according to U.S. Pat. No. 5,158,526. Finally, the third one was a placebo sole, made, as the other test soles, by gluing together two semi-rigid leather layers, but with no active principle placed between both layers at the level of the arch.

Experimental procedures:

Both studies A and B were prospective, placebo-controlled, double-blind studies. Each selected patient was subjected to 3 consecutive treatments in study A and 4 consecutive treatments in study B. Each treatment consisted in applying a pair of soles, together with a pair of socks and a pair of shoes to the feet of the patient, according to the following experimental plan:

Study A
- Treatment 1: placebo sole, in contact with the foot skin
- Treatment 2: polarizing sole, in contact with the foot skin
- Treatment 3: sulphur sole, in contact with the foot skin Study B
- Treatment 1: placebo sole, under the socks
- Treatment 2: polarizing sole, under the socks
- Treatment 3: sulphur sole, under the socks
- Treatment 4: sulphur sole, in contact with the foot skin.

The blindness of the studies was ensured by the following procedures:

the treatments and the clinical evaluation were performed by two different persons, located in different rooms. In these conditions, the clinician performed clinical evaluations on patients wearing shoes and socks, ensuring the blindness of the clinical examination. In addition, all three types of soles were indistinguishable and coded, so that the technician responsible for the treatments could not know the nature of the sole he was using. Finally, in each study, all 3 or 4 treatments were administered in a random sequence, differing for each patient.

Clinical Evaluation:

Following each treatment, the patient was subjected to a clinical evaluation, that included:

pelvic tilt: detected by a visual examination and a palpation of the pelvis;

shoulder imbalance: detected by a visual examination and palpation of the shoulders, and quantified by the following test: patient in standing position, both arms dangling; the clinician joins both hands and measures the distance (cm) between both forefingers;

pectoral girdle rotation: detected and quantified by the following test: patient in standing position, raises both arms parallel, the clinician joins both hands and measures the distance (cm) between both forefingers.

Statistical Analysis:

The relative efficacies of the different treatments within each study were evaluated by comparing:

1—the effects of the treatments on the number of pelvic tilts, shoulder imbalances and rotations completely corrected, by McNemar tests;

2—the effects of the treatments on the intensities of shoulder imbalances and rotations, by an ANOVA analysis of variance for repeated measures. When normality test did not pass, a repeated measure ANOVA on rank was run.

Results

Study A

As shown in Table I, the results revealed that both the polarizing and the sulphur soles completely resolved a similar number of imbalances and rotations when applied at the foot skin contact. Both treatments were significantly more efficient than the placebo treatment. However, as illustrated in Table II, the sulphur soles was significantly better than the polarizing soles (P<0.05) with respect to their effects on the intensities of the shoulder imbalances and rotations. Namely, the polarizing soles decreased imbalances and rotations intensities by 61% and 73%, respectively, when compared to the placebo soles, whereas sulphur soles decreased imbalances and rotations intensity by 67% and 86%, respectively.

Study B

As shown in Tables III and IV, when applied under cotton socks, the polarizing soles had a very weak effect on statural parameters. These soles did not succeed in completely resolving imbalances or rotations except for 2 pelvic tilts (Table III). Moreover, they exhibited a very low potency, decreasing the intensities of shoulder imbalances and rotations by 15% and 18% respectively. In contrast, the sulphur soles were equipotent, whether applied under socks or directly applied at the foot skin contact, and reduced the intensities of shoulder imbalances and rotations by 72% and 72%, respectively, when applied under socks (Table IV). When applied under socks, the sulphur soles were statistically more potent than the polarizing soles with respect to all measured parameters (Tables III and IV).

In conclusion, the results of both these studies showed that the sulphur soles, which are one of the preferred embodiment of the present invention:

1) were more potent than the polarizing soles in improving statural parameters when applied directly at the contact of the foot skin; and 2) retained their full potency when applied under socks, in contrast to the polarizing soles, that lost almost completely their activity.

TABLE I

Study A: number of imbalances and rotations completely resolved following applications of the tested soles.

| | pelvic tilts | shoulder imbalances | shoulder rotations |
|---|---|---|---|
| placebo soles at the skin contact | 0/24 | 0/24 | 0/24 |
| polarizing soles at the skin contact | 18/24 (a) | 7/24 (a) | 13/24 (a) |
| sulphur soles at the skin contact | 20/24 (a) | 8/24 (a) | 17/24 (a) |

(a) $P < 0.05$ when compared to the placebo soles

TABLE II

Study A: effect of the tested soles on the intensity of shoulder imbalances and rotations (mean ± SEM of 24 patients).

| | Shoulder imbalances | Shoulder rotations |
|---|---|---|
| placebo soles at the skin contact | 2.06 ± 0.11 | 1.60 ± 0.12 |
| polarizing soles at the skin contact | 0.81 ± 0.13 (a) | 0.43 ± 0.11 (a) |
| sulphur soles at the skin contact | 0.68 ± 0.55 (a,b) | 0.23 ± 0.08 (a,b) |

(a) $P < 0.05$ when compared to the placebo soles
(b) $P < 0.05$ when compared to the polarizing soles

TABLE III

Study B: number of tilts and rotations completely resolved following applications of the tested soles.

| | pelvic tilts | shoulder imbalances | shoulder rotations |
|---|---|---|---|
| placebo soles under socks | 0/16 | 0/16 | 0/16 |
| polarizing soles under socks | 2/16 | 0/16 | 0/16 |

TABLE III-continued

Study B: number of tilts and rotations
completely resolved following applications of
the tested soles.

|  | pelvic tilts | shoulder imbalances | shoulder rotations |
|---|---|---|---|
| sulphur soles under socks | 12/16 (a,b) | 7/16 (a,b) | 8/16 (a,b) |
| sulphur soles at the skin contact | 11/16 (a,b) | 7/16 (a,b) | 7/16 (a,b) |

(a) P < 0.05 when compared to the placebo soles
(b) P < 0.05 when compared to the polarizing soles

TABLE IV

Study B: effects of the tested soles on the
intensities of shoulder imbalances rotations
(mean ± SEM of 16 patients)

|  | Shoulder imbalances | Shoulder rotations |
|---|---|---|
| placebo soles under socks | 1.98 ± 0.14 | 2.04 ± 0.17 |
| polarizing soles under socks | 1.68 ± 0.14 (a) | 1.68 ± 0.17 (a) |
| sulphur soles under socks | 0.56 ± 0.16 (a,b) | 0.58 ± 0.16 (a,b) |
| sulphur soles at the skin contact | 0.61 ± 0.17 (a,b) | 0.72 ± 0.20 (a,b) |

(a) P < 0.05 when compared to the placebo soles
(b) P < 0.05 when compared to the polarizing soles

EXAMPLE II

Effect of Mineral-containing Insoles on Pain and Quality of Life in Patients with Chronic Back Pain a Randomized Placebo Controlled, Double-blind Study The objective of this clinical study was to determine the long-term beneficial effect of mineral-containing insoles in patients with chronic back pain. The tested insoles contained a combination of 8 different crystals of minerals as described in the preferred embodiments of the present invention.

With regards to the choice of parameters to measure to evaluate treatment efficacy, there is growing recognition that patient perspectives are essential. Back pain is one of many chronic or recurrent condition for which cure may be impossible, and improving quality of life is often the main goal of therapy. Therefore, we evaluated the effect of a 6-week treatment with the mineral-containing insoles on patient's quality of life assessed by a validated questionnaire, specifically designed to measure self-rated disability due to back pain.

Materials and Methods

Patients:

A total of 35 patients were included in the protocol. Selected patients ranged between 18 and 65 years of age, and had chronic back pain, which was defined as back pain present on at least half of the days in a 12-month period in a single or in multiple episodes over the year. The patients were included in the study only if they had a score of at least 6 in the Roland and Morris questionnaire (see below for description). None of the patients had worn any kind of medical insole in the previous 6 months. All the patients gave informed consent to participate in the study.

Treatments:

The patients were randomly assigned to two treatment groups in a 2:1 ratio (2 mineral insoles for 1 placebo sole). The mineral-containing insoles were insoles in which a combination of seven different minerals with selected colors (red jasper, orange cornelian, yellow topaz safranite, green aventurine, blue azurite, purple amethyst and white quartz) was inserted as seven lines transversely between the two semi-rigid fabric layers used to manufacture the sole, according to the drawings in FIGS. 5 and 6 of the present invention; in addition, an amount of 50 to 100 mg sulphur powder was placed at the level of the arch, according to FIGS. 3 and 4 of the present invention. The placebo soles were manufactured using the same raw materials, except for the minerals and sulphur powder, which were substituted by sugar. Both placebo and mineral insoles were indistinguishable and coded to ensure the blindness of the study.

Measures:

On the day of inclusion in the study and 6 weeks later, the patients were asked to fill the Roland and Morris questionnaire, which is a validated 24-item questionnaire designed to measure self-rated disability due to back pain (Roland M and Morris R, Spine 8:141–144, 1983). In this questionnaire, the score of the patient is defined as the number of items for which the patient answers "yes" and ranges therefore between 0 (no disability) and 24 (maximum disability).

Statistical analysis:

The Roland and Morris scores, measured in each patient before and after 6 weeks of treatment were subjected to a two-way ANOVA analysis for repeated measures, with factors of variation being time (before vs. after treatment) and treatment (placebo vs. mineral insoles). When statistical significance was reached, multiple comparisons were performed using the Student-Newman-Keuls method. P<0.05 was considered statistically significant.

Results and Discussion

Figure 7:
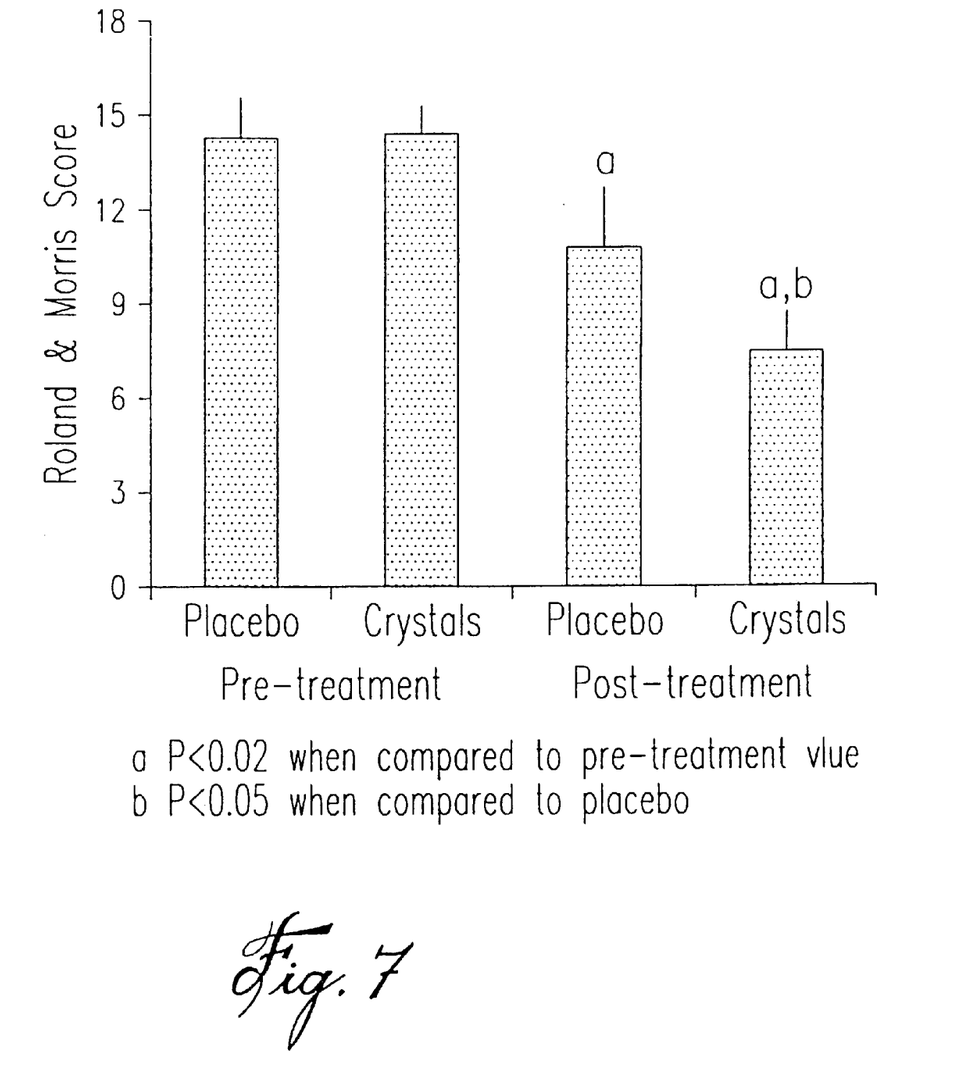
FIG. 7 is a graph of the Roland and Morris statistical analysis of patient's measurements before and after treatment.

A total of 35 patients were included in the study and were randomized into a placebo group (11 patients) and a mineral insole group (24 patients). As shown in FIG. 7, both groups had a similar initial score (mean+SEM: placebo 14.27±1.25 vs. minerals 14.38±0.85, NS). After 6 weeks of treatment, the score was significantly improved in both groups. The score was decreased by 25% in the placebo group to 10.73±2.05 (P<0.02), whereas it was decreased by 49% in the mineral insoles group to 7.50±1.18 (P<0.01). The 49% improvement observed in the mineral insoles group was statistically greater than the 25% improvement observed in the placebo group (P<0.05).

These results show that the mineral containing insoles significantly improved the quality of life of patients with chronic back pain by decreasing their disability condition by 49%. The observed placebo effect (25%) is not surprising in such a clinical study where subjective parameters are measured such as pain, well-being or quality of life. This emphasizes the need to implement double-blind, placebo-controlled studies to evaluate the clinical efficacy of new treatments for chronic back pain.

In conclusion, the mineral insoles are powerful tools that can be used therapeutically to improve the condition of patients with chronic back pain.

EXAMPLE III

Clinical Usefulness of the Mineral Insoles of the Present Invention

Numerous experimental and scientific data suggest that the foot sole is the starting point for neurophysiological pathways responsible for the control of body posture. The role of these exteroceptive and proprioceptive pathways is to control the tone of the muscular chains controlling the equilibrium.

The efficacy of a new technology, comprising of placing a combination of selected minerals under the foot sole has been demonstrated in previous Examples I and II. Namely, these studies, which were run in placebo-controlled, double blind conditions, have shown that the tested mineral insoles were capable of treating most of pelvic tilts and shoulder slumps, and that the continuous use of such insoles significantly improved the condition of patients with chronic back pain. The observations that the application of the insoles have an immediate effect on body posture strongly indicate that they very likely act by interfering with the neurophysiological pathways involving the exteroceptive and proprioceptive receptors of the foot sole.

The goal of the present study was to demonstrate the clinical usefulness of the mineral insoles for chiropractors and other healthcare professionals who routinely treat patients with musculo-skeletal pain. The specific objectives were 1) to determine the prevalence of postural imbalances among chiropractic patients and 2) to measure the postural efficacy of the mineral insoles in these patients using a new scoring system for the evaluation of body posture.

Materials and Methods

Patients

A total of 96 patients, men and women, aged 10 to 80 years, were selected in two chiropractic clinics. Most of them consulted a chiropractor for musculo-skeletal pain, including back pain, whereas some presented other syndromes such as chronic headache or vertigoes. None of the selected patients had received a chiropractic adjustment in the last 3 months.

The Postural Scoring Scale

A new scoring system was developed and used for the need of the present study. In this scoring system, the posture is assessed from 4 different clinical parameters, each of these parameters having a score from 0 to 2:

Pelvic tilts: the physician reports any unevenness of right and left iliac crests, and anterior superior and posterior superior iliac spines by palpation (score: no tilt: 0; small tilt: 1; serious tilt: 2)

Shoulder slump (tilt): the physician determines shoulder imbalance by detecting any difference in the height of the right and left clavicles. A quantitative measure is obtained by asking the patient to keep both arms dangling, then bringing both hands together and measuring the distance (cm) between the tips of both indexes. (Score: tilt less than 1 cm: 0; tilt exceeding 1 cm: 1: tilt exceeding 2 cm: 2).

Shoulder Rotation: the physician measures the intensity of any shoulder rotation by asking the patient to horizontally extend the arms straight ahead, at shoulder's height, fingers in extension, then bringing both hands together and finally measuring the distance between the tips of both indexes.(Score: rotation less than 1 cm: 0; rotation exceeding 1 cm: 1: rotation exceeding 2 cm: 2).

Amplitude of head rotation: the physician positions himself behind the patient and places his hands on the patient's shoulders to limit shoulder's movements. Then he asks the patient to turn the head on both sides and evaluate the amplitude of rotation by asking whether the patient can see his face and eyes (Score: patient sees examiner's eyes: 0; patient sees only examiner's face, but not eyes: 1; patient does not see examiner's face: 0).

Finally, the scores of each separate parameters are added and the total score therefore ranges between 0 (no postural imbalance) to 8 (severe postural imbalance).

Experimental Procedures

On the day of chiropractic examination, and before any adjustment performed by the chiropractor, each patient was subjected to two consecutive postural evaluations. The first one was a basal evaluation (without insoles), and the second one was performed within 1 minute following the insertion of test mineral insoles. The mineral insoles were insoles in which a combination of seven different minerals with selected colors (red jasper, orange cornelian, yellow topaz safranite, green aventurine, blue azurite, purple amethyst and white quartz) was inserted as seven lines transversely between the two semi-rigid fabric layers used to manufacture the sole, according to FIGS. 5 and 6; in addition, an amount of 50 to 100 mg sulphur powder was placed at the level of the arch, according to FIGS. 3 and 4. In the postural evaluation, with or without the test insoles, the patients were allowed to keep their socks or stockings, since previous studies have shown that the mineral insoles are equally effective whether placed at the direct contact of the foot sole skin or under socks or stockings (see example 1), in contrast to the prior art (Bricot, U.S. Pat. No. 5,158,526).

Data Analysis

The postural scores, measured in each patient with (basal score) and without (mineral score) the mineral test insoles, were subjected to a Friedman repeated measures analysis of variance on ranks, a non-parametric test, since the data did not follow the criteria of statistical normality. Multiple comparisons (basal vs mineral scores) were performed using the Dunn's method. In parallel, the effect of the mineral insoles on each specific measured parameter (tilts, rotations) was evaluated by running McNemar tests.

Results and Discussion

Basal Postural Parameters in a Population of Patients with Various Types of Musculo-skeletal Pain The basal postural evaluation revealed that, among the 96 tested patients, 91 (or 95%) had a pelvic tilt, 94 (or 98%) had a shoulder slump, 83 (or 86%) had a shoulder rotation and 86 (or 90%) had a decreased amplitude of head rotation. No patient had a perfectly balanced posture, as none of them exhibited a total score of 0. The distribution of the total basal score of these patients is shown in Table V.

TABLE V

Distribution of the 96 patients as a function of their basal postural score

| Postural Score | 2 | 3 | 4 | 5 | 6 | 7 | 8 |
|---|---|---|---|---|---|---|---|
| Number of patients | 3 | 3 | 20 | 24 | 23 | 19 | 4 |

These observations show that all the selected patients had minor to severe postural imbalances. Whether these imbalances are related to the musculo-skeletal pain remains to be investigated by comparing the posture of patients with or without pain. In addition, the scoring scale tested was well adapted for the need of the study, since a majority of the patients exhibited scores of 4, 5, 6, i.e. in the middle of the scale.

Postural Effect of the Mineral Insoles

Figure 8:
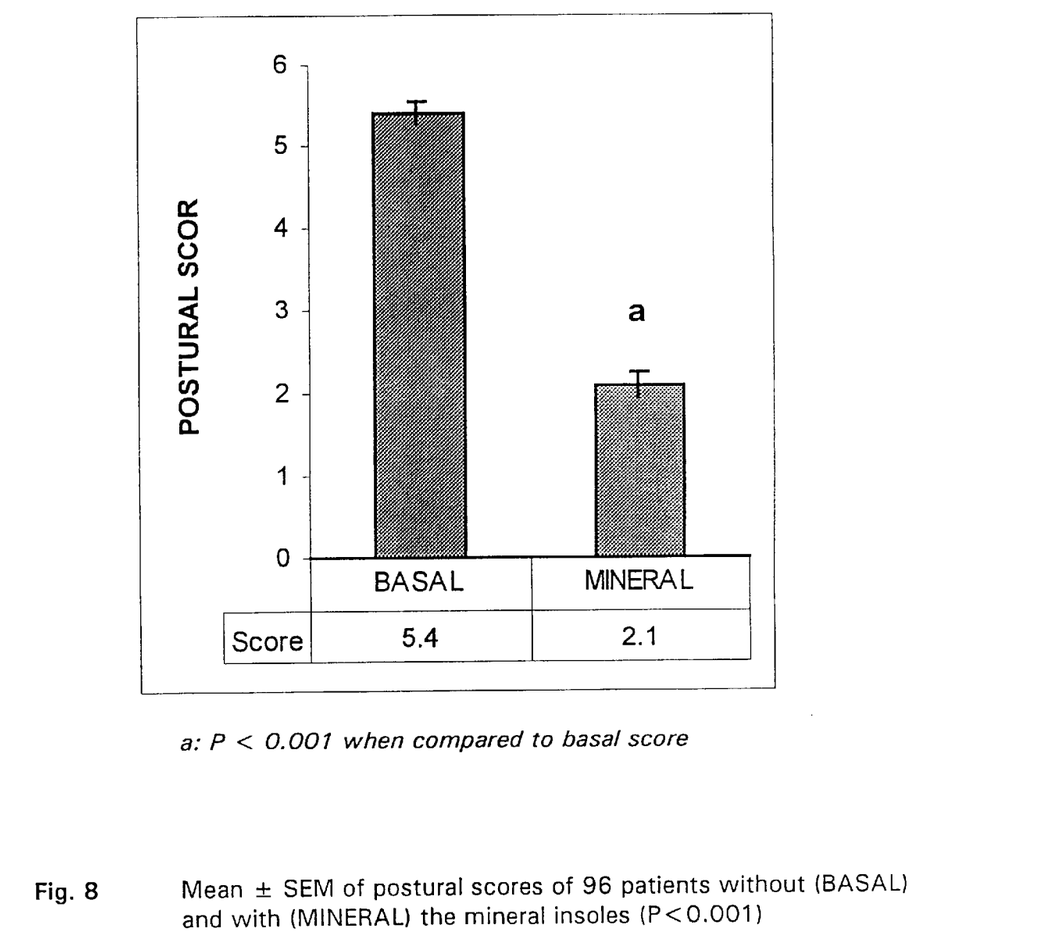
FIG. 8 is a graph showing the highly significant effect of the mineral insoles on the postural score of 96 patients in a chiropractic clinic.

As shown in FIG. 8, the average basal postural score in the 96 patients was 5.40±0.14, and this score was decreased by 61.3% to 2.09±0.15 with the mineral test insoles (P<0.001). In addition, as shown in Table VI, the mineral insoles successfully improved all tested postural parameters. The mineral insoles were most efficient on pelvic tilts (81.7% of pelvic tilts were improved or completely corrected), but were also highly active to improve shoulder tilts and rotations, as well as amplitude of head rotation.

TABLE VI

Number of patients improved for each separate measured postural parameter following insertion of the mineral insoles

|  | No improvement (n) | Improvement (n) | % patients improved |
| --- | --- | --- | --- |
| Pelvic tilts (n = 91) | 14 | 77 | 84.6% (P < 0.001) |
| Shoulder tilts (n = 94) | 23 | 71 | 75.5% (P < 0.001) |
| Shoulder Rotations (n = 83) | 33 | 50 | 60.2% (P < 0.001) |
| Head amplitude (n = 86) | 21 | 55 | 64.0% (P < 0.001) |

In conclusion, the results of this study demonstrated that all patients tested exhibited postural imbalance, and that the mineral insoles were highly effective in treating these imbalances. These results underscore the usefulness of this new device, that fulfill a therapeutic need in those patients who a health care professional for musculo-skeletal problems.

EXAMPLE IV

The goal of this study was to determine whether the postural effect of the mineral insoles (as reported in examples 1 and 3) is complementary to the chiropractic treatment.

The procedures were conducted a described in "Materials and Methods" of Example 3, except that the postural tests, with and without mineral insoles, were performed before and after one month of intensive chiropractic treatment, defined as 3 adjustment sessions per week on a 4 week-period. A total of 22 patients were included and completed the study.

Figure 9:
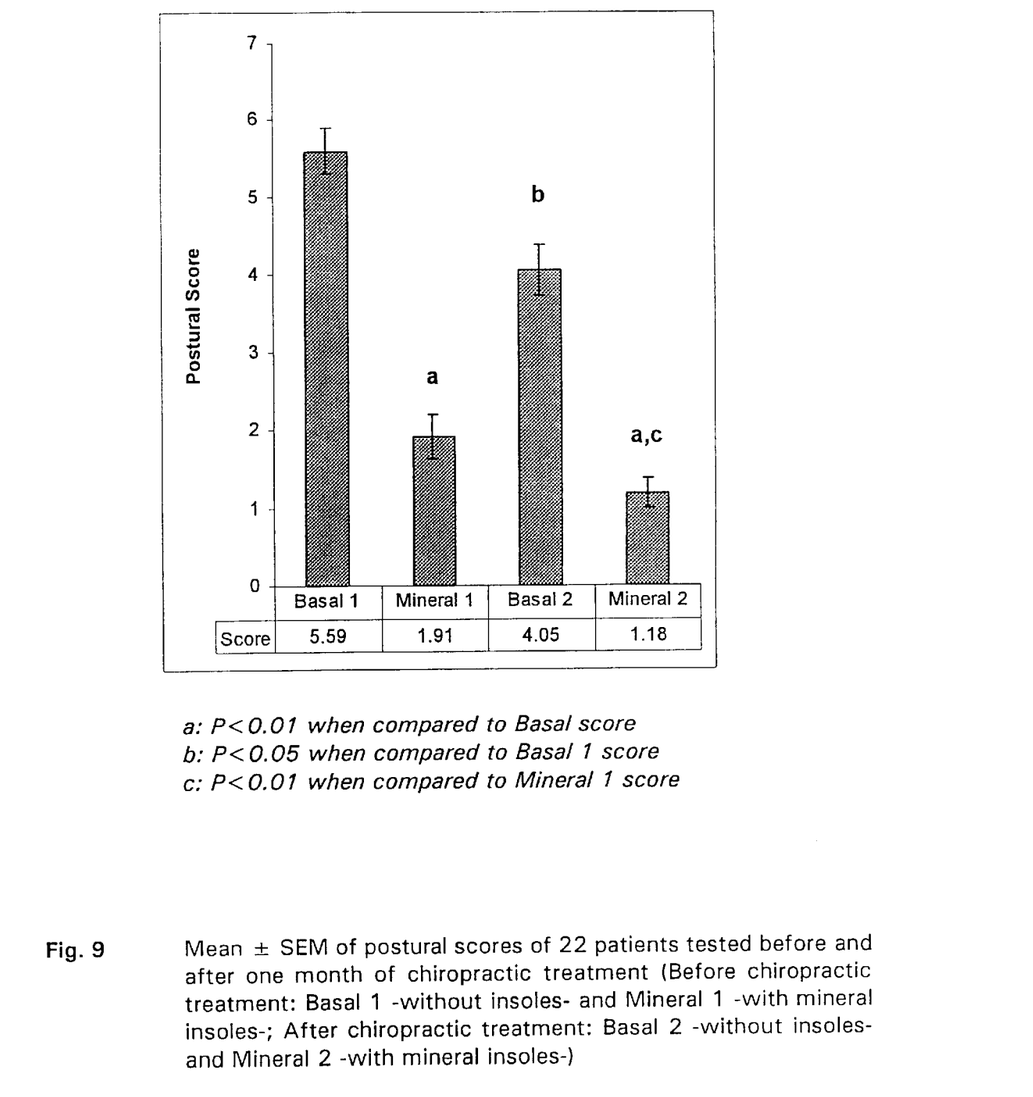
FIG. 9 is a graph demonstrating the additive effects of the mineral insoles and the chiropractic treatment on patient's postural score.

As shown in FIG. 9, the statistical analysis of the data indicated an interaction between the chiropractic treatment and the acute postural effect of the mineral insoles. Namely, the basal postural score (without insoles) was significantly decreased after one month of chiropractic treatment from 5.59±0.30 to 4.05±0.33 (a 27.5% improvement, P<0.05). The mineral insole induced a highly significant postural effect, both before and after one month of chiropractic treatment (65.8% and 70.9% improvement, respectively, P<0.01). In addition, the "mineral score", i.e. the postural score with the mineral insole was significantly lower after vs before the chiropractic treatment (1.91±0.28 vs 1.18±0.19, a 38.2% improvement, P<0.01). The best postural score was obtained only with the combination of both the chiropractic treatment and the use of the mineral insoles.

In conclusion, these data show that the use of the mineral insole as a postural balancer is complementary to the chiropractic treatment on the patient's body posture. Both treatment very likely act by different and complementary neurophysiological mechanisms.

Although the invention has been described with respect to specific embodiments, it is understood that modifications are possible within the scope of the appended claims without departing from the spirit of the invention.

We claim:

1. Pedal device for treating and/or preventing physical troubles associated with statural disequilibrium, which comprises an article adapted to contact a sole of a foot, said article incorporating within two layers at least one unoriented mineral for stimulating reflex zones located at the sole of the foot, whereby said unoriented mineral does not act as a polarizer.

2. Pedal device according to claim 1; wherein said unoriented mineral is in powder form.

3. Pedal device according to claim 1, wherein said article comprises an inner sole to be worn against said sole of a foot.

4. Pedal device according to claim 1, wherein said inner sole is an inner sole of a shoe.

5. Pedal device according to claim 1, wherein said article comprises two semi-rigid fabric layers bonded together, said substance being inserted between said layers of said foot sole.

6. Pedal device according to claim 5, wherein said unoriented mineral substance is selected from the group consisting of crystals and powders selected from elements, natural and synthetic sulfides and sulfosalts, natural and synthetic halides, natural and synthetic oxides and hydroxides, natural and synthetic nitrates, carbonates and borates, natural and synthetic sulfates, chromates, molybdates and tungstates, natural and synthetic phosphates, arseniates, and vanadates, natural and synthetic silicates, and natural and organic substances.

7. Pedal device according to claim 5, wherein said unoriented mineral substance is selected from the group consisting of sulphur powders.

8. Pedal device according to claim 5, wherein said unoriented mineral is a combination of the following different colors: red, orange, yellow, green, blue, purple and white.

9. Pedal device according to claim 8, wherein said unoriented mineral substance is selected from the group consisting of jasper, cornelian, topaz safranite, aventurine, azurite, amethyst and quartz and mixtures thereof.

10. Pedal device according to claim 5, wherein said unoriented mineral substance is disposed between said layers as a plurality of transverse bands of said unoriented mineral substances.

11. Pedal device according to claim 1, wherein said unoriented mineral substance comprises powdered sulphur, said powdered sulphur being incorporated between said fabric layers in amount between about 5 mg to 30 g, at the level of an arch of said foot sole.

12. Pedal device according to claim 11, wherein said unoriented mineral comprises a mixture of sulphur powder, red jasper, orange cornelian, yellow topaz safranite, green aventurine, blue azurite, purple amethyst and white quartz.

13. Pedal device for treating and/or preventing physical troubles associated with statural disequilibrium, which comprises an article adapted to contact a sole of a foot, said article incorporating between two semi-rigid bonded layers at least one unoriented mineral selected from the group consisting of sulfur powders, jasper, cornelian, topaz safranite, aventurine, azurite, amethyst and quartz for stimulating reflex zones located at the sole of the foot, whereby said unoriented crystalline substance does not act as a polarizer.

14. Method for treating and/or preventing physical troubles associated with statural disequilibrium which comprises placing a pedal device at one or both feet of a person in need of correction of statural disequilibrium, said pedal device comprising an article adapted to contact a sole of a foot, said article incorporating within two layers at least one unoriented mineral selected from the group consisting of sulfur powders, jasper, cornelian, topaz safranite, aventurine, azurite, amethyst and quartz for stimulating reflex zones located at the sole of the foot, whereby treating and/or preventing physical troubles associated with statural disequilibrium, whereby said unoriented crystalline substance does not act as a polarizer.

15. The method of claim 14, which further comprises placing a pedal device at one or both feet of said patient.

16. The method of claim 14, wherein the preventing physical troubles associated with statural disequilibrium is musculoskeletal pain.

17. The method of claim 14, wherein the musculoskeletal pain is chronic back pain.

18. The method of claim 14, wherein said pedal device is applied directly to skin of said sole foot.

19. The method of claim 14, wherein said pedal device is placed over socks or stockings worn by said patient.

20. Method for improving muscle strength and physical performance which comprises placing a pedal device at one or both feet of a person in need of correction of statural disequilibrium, said pedal device comprising an article adapted to contact a sole of a foot, said article incorporating within two layers at least one unoriented mineral selected from the group consisting of sulfur powders, jasper, cornelian, topaz safranite, aventurine, azurite, amethyst and quartz for stimulating reflex zones located at the sole of the foot, whereby treating and/or preventing physical troubles associated with statural disequilibrium, whereby said unoriented mineral does not act as a polarizer.

21. Method for inducing stress relief which comprises placing a pedal device at one or both feet of a person in need of correction of statural disequilibrium, said pedal device comprising an article adapted to contact a sole of a foot, said article incorporating within two layers at least one unoriented mineral selected from the group consisting of sulfur powders, jasper, cornelian, topaz safranite, aventurine, azurite, amethyst and quartz for stimulating reflex zones located at the sole of the foot, whereby treating and/or preventing physical troubles associated with statural disequilibrium, whereby said unoriented mineral does not act as a polarizer.

* * * * *